US008048040B2

(12) United States Patent
Kiani

(10) Patent No.: US 8,048,040 B2
(45) Date of Patent: Nov. 1, 2011

(54) FLUID TITRATION SYSTEM

(75) Inventor: Massi E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 151 days.

(21) Appl. No.: 12/208,998

(22) Filed: Sep. 11, 2008

(65) Prior Publication Data

US 2009/0076462 A1  Mar. 19, 2009

Related U.S. Application Data

(60) Provisional application No. 60/993,584, filed on Sep. 13, 2007.

(51) Int. Cl.
*A61M 5/00* (2006.01)
*A61B 5/00* (2006.01)

(52) U.S. Cl. ........................ 604/246; 600/310
(58) Field of Classification Search ................ 604/246, 604/66; 600/310
See application file for complete search history.

(56) References Cited

U.S. PATENT DOCUMENTS

| | | | |
|---|---|---|---|
| 4,109,643 A * | 8/1978 | Bond et al. ..................... 600/479 |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,111,817 A * | 5/1992 | Clark et al. ..................... 600/323 |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |

(Continued)

*Primary Examiner* — Kevin C Sirmons
*Assistant Examiner* — Michael J Anderson
(74) *Attorney, Agent, or Firm* — Knobbe, Martens, Olson & Bear LLP

(57) ABSTRACT

A fluid titration system has an optical sensor, a physiological monitor, a titration controller and an infusion device. The optical sensor transmits multiple wavelengths of light into a tissue site of a person and detects the optical radiation after attenuation by pulsatile blood flowing within the tissue site. The physiological monitor receives a resulting sensor signal and derives a plethysmograph that corresponds to the pulsatile blood flow. The monitor also calculates a plethysmograph variability measure that is responsive to changes in perfusion at the tissue site. A titration controller generates a fluid control output according to the variability measure. The infusion device administers a liquid solution via an intravenous (IV) connection to the person according to the fluid control output so as to regulate at least one of a fluid flow start, rate and stop.

20 Claims, 8 Drawing Sheets

U.S. PATENT DOCUMENTS

| | | | |
|---|---|---|---|
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,766,127 A * | 6/1998 | Pologe et al. | 600/310 |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,165,151 A * | 12/2000 | Weiner | 604/66 |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,321,100 B1 | 11/2001 | Parker | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Diab et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-All | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,067,893 B2 | 6/2006 | Mills et al. | |
| 7,096,052 B2 | 8/2006 | Mason et al. | |
| 7,096,054 B2 | 8/2006 | Abdul-Hafiz et al. | |
| 7,132,641 B2 | 11/2006 | Schulz et al. | |
| 7,142,901 B2 | 11/2006 | Kiani et al. | |
| 7,149,561 B2 | 12/2006 | Diab | |
| 7,186,966 B2 | 3/2007 | Al-Ali | |
| 7,190,261 B2 | 3/2007 | Al-Ali | |
| 7,215,984 B2 | 5/2007 | Diab | |
| 7,215,986 B2 | 5/2007 | Diab | |
| 7,221,971 B2 | 5/2007 | Diab | |
| 7,225,006 B2 | 5/2007 | Al-Ali et al. | |
| 7,225,007 B2 | 5/2007 | Al-Ali | |
| RE39,672 E | 6/2007 | Shehada et al. | |
| 7,239,905 B2 | 7/2007 | Kiani-Azarbayjany et al. | |
| 7,245,953 B1 | 7/2007 | Parker | |
| 7,254,431 B2 | 8/2007 | Al-Ali | |
| 7,254,433 B2 | 8/2007 | Diab et al. | |
| 7,254,434 B2 | 8/2007 | Schulz et al. | |

| | | | | | | |
|---|---|---|---|---|---|---|
| 7,272,425 | B2 | 9/2007 | Al-Ali | 7,355,512 B1 | 4/2008 | Al-Ali |
| 7,274,955 | B2 | 9/2007 | Kiani et al. | 7,371,981 B2 | 5/2008 | Abdul-Hafiz |
| D554,263 | S | 10/2007 | Al-Ali | 7,373,193 B2 | 5/2008 | Al-Ali et al. |
| 7,280,858 | B2 | 10/2007 | Al-Ali et al. | 7,373,194 B2 | 5/2008 | Weber et al. |
| 7,289,835 | B2 | 10/2007 | Mansfield et al. | 7,376,453 B1 | 5/2008 | Diab et al. |
| 7,292,883 | B2 | 11/2007 | De Felice et al. | 7,377,794 B2 | 5/2008 | Al Ali et al. |
| 7,295,866 | B2 | 11/2007 | Al-Ali | 7,377,899 B2 | 5/2008 | Weber et al. |
| 7,328,053 | B1 | 2/2008 | Diab et al. | 7,383,070 B2 | 6/2008 | Diab et al. |
| 7,332,784 | B2 | 2/2008 | Mills et al. | 7,415,297 B2 | 8/2008 | Al-Ali et al. |
| 7,340,287 | B2 | 3/2008 | Mason et al. | 2005/0010166 A1* | 1/2005 | Hickle ............... 604/66 |
| 7,341,559 | B2 | 3/2008 | Schulz et al. | 2005/0177096 A1* | 8/2005 | Bollish et al. .......... 604/65 |
| 7,343,186 | B2 | 3/2008 | Lamego et al. | * cited by examiner | | |
| D566,282 | S | 4/2008 | Al-Ali et al. | | | |

FLUID TITRATION SYSTEM

REFERENCE TO RELATED APPLICATION

The present application claims priority benefit under 35 U.S.C. §119(e) from U.S. Provisional Application No. 60/993,584, filed Sep. 13, 2007, entitled "Fluid Titration System," which is incorporated herein by reference.

BACKGROUND OF THE INVENTION

FIG. 1 illustrates a physiological monitoring system 100 having a physiological monitor 120, a noninvasive sensor 130 attached to a tissue site 1, and a sensor cable 140 interconnecting the monitor 120 and the sensor 130. Physiological monitoring systems for measuring constituents of circulating blood have gained rapid acceptance in a wide variety of medical applications, including surgical wards, intensive care and neonatal units, general wards, home care, physical training, and virtually all types of monitoring scenarios. The noninvasive sensor 130 has light emitting diodes (LEDs) and a detector. The LEDs transmit optical radiation into the tissue site 1, and the detector responds to the intensity of the optical radiation after absorption by pulsatile blood flow within the tissue site. Based upon this response, the physiological monitor 120 determines measurements for physiological parameters. The physiological monitoring system 100 may incorporate pulse oximetry, which is a widely accepted noninvasive procedure for measuring physiological parameters, such as oxygen saturation and pulse rate among others. The physiological monitoring system 100 may also incorporate advanced features, such as a multiple wavelength sensor and advanced processes for determining other physiological parameters, such as carboxyhemoglobin, methemoglobin and total hemoglobin, as a few examples. The physiological monitor 120 displays the physiological parameters and typically provides visual and audible alarm mechanisms that alert a caregiver when these parameters are outside of predetermined limits.

Pulse oximeters capable of reading through motion induced noise are disclosed in at least U.S. Pat. Nos. 6,770,028, 6,658,276, 6,650,917, 6,157,850, 6,002,952, 5,769,785, and 5,758,644; low noise pulse oximetry sensors are disclosed in at least U.S. Pat. Nos. 6,088,607 and 5,782,757; all of which are assigned to Masimo Corporation, Irvine, Calif. ("Masimo") and are incorporated by reference herein.

Physiological monitors and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Masimo Laboratories, Irvine, Calif. (Masimo Labs) and both incorporated by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and RAD-57™ and Radical-7™ monitors for measuring $SpO_2$, pulse rate, perfusion index, signal quality, HbCO and HbMet among other parameters are also available from Masimo.

FIG. 2 illustrates the standard plethysmograph waveform 200, which can be derived from a pulse oximetry system, as described above. The plethysmograph waveform 200 illustrates light absorption at the tissue site, shown along the y-axis 10, versus time, shown along the x-axis 20. The total absorption includes components of static absorption 210 and variable absorption 220. Static absorption 210 is due to tissue, venous blood and a base volume of arterial blood. Variable absorption 220 is due to the pulse-added volume of arterial blood. That is, the plethysmograph waveform 200 is a visualization of the tissue site arterial blood volume change over time, and is a function of heart stroke volume, pressure gradient, arterial elasticity and peripheral resistance. The ideal waveform pulse 230 displays a broad peripheral flow curve, with a short, steep inflow phase 232 followed by a 3 to 4 times longer outflow phase 234. The inflow phase 232 is the result of tissue distention by the rapid blood volume inflow during ventricular systole. During the outflow phase 234, blood flow continues into the vascular bed during diastole. The plethysmograph baseline 240 indicates the minimum basal tissue perfusion.

SUMMARY OF THE INVENTION

FIG. 3 illustrates a hypovolemic plethysmograph waveform 300, i.e. a plethysmograph displaying characteristics of a person having an abnormal decrease in blood volume. Hypovolemia is often caused from blood loss during surgery or due to an injury. Under hypovolemic conditions, a respiration-induced cyclical variation occurs in a plethysmograph baseline 340. In particular, the baseline 340 varies with a period corresponding to the respiration rate 350. This cyclical variation is particularly evident in patients undergoing positive ventilation. The amount of cyclical variation correlates to a person's blood volume, i.e. the less blood volume the greater the cyclical variation in the plethysmograph waveform. Accordingly, a measure of plethysmograph variation may be indicative of hypovolemic conditions.

FIG. 4 illustrates a plethysmograph 400 plotted on an amplitude axis 30 versus a time axis 40. As described above, the amplitude may be responsive to light absorption of pulsatile blood flow with a person's tissue. The plethysmograph 400 has multiple pulses 460 each with a peak 462 and a valley 464 and extending over a time period 466. A perfusion index (PI) value can be defined for each pulse 460:

$$PI = AC/DC \quad (1)$$

where "AC" 454 designates a peak amplitude 462 minus a valley amplitude 464 for a particular pulse and where "DC" 456 designates a peak amplitude 462 for a particular pulse. In an embodiment, an IR channel plethysmograph from a detector response to an IR wavelength LED is utilized to calculate PI. A plethysmograph variability index (PVI) is then calculated that is responsive to variations in perfusion index, as described below.

In an embodiment, PVI calculations utilize only PI values resulting from acceptable plethysmograph pulses. For example, a red channel plethysmograph responsive to a red wavelength LED is used to verify acceptable pulses in the IR channel. Physiological plethysmograph identification is disclosed in U.S. Pat. No. 7,044,918 titled Plethysmograph Pulse Recognition Processor, which is incorporated by reference herein. PVI values are calculated from a sorted and trimmed buffer representing a sliding time window of PI values. The sort orders the PI values from the minimum PI at one end of the buffer to the maximum PI at the other end of the buffer. A predetermined number of both maximum and minimum PIs are deleted from each end of the buffer and PVI is calculated as:

$$PVI = [(PI_{MAX} - PI_{MIN})/PI_{MAX}] \times 100 \quad (2)$$

That is, PVI is the PI variation, expressed as a percentage of the difference between the maximum and minimum PIs remaining in the buffer. In an embodiment, a median PVI is calculated from PVIs stored in a second buffer. PVI is described in U.S. Provisional Patent App. No. 60/873,663 filed Dec. 9, 2006 titled Plethysmograph Variability Index, incorporated by reference herein. A PVI enabled physiological monitor advantageously provides a noninvasive numerical measure of hypovolemic conditions so as to titrate patient fluids.

DETAILED DESCRIPTION OF THE PREFERRED EMBODIMENT

Figure 1:
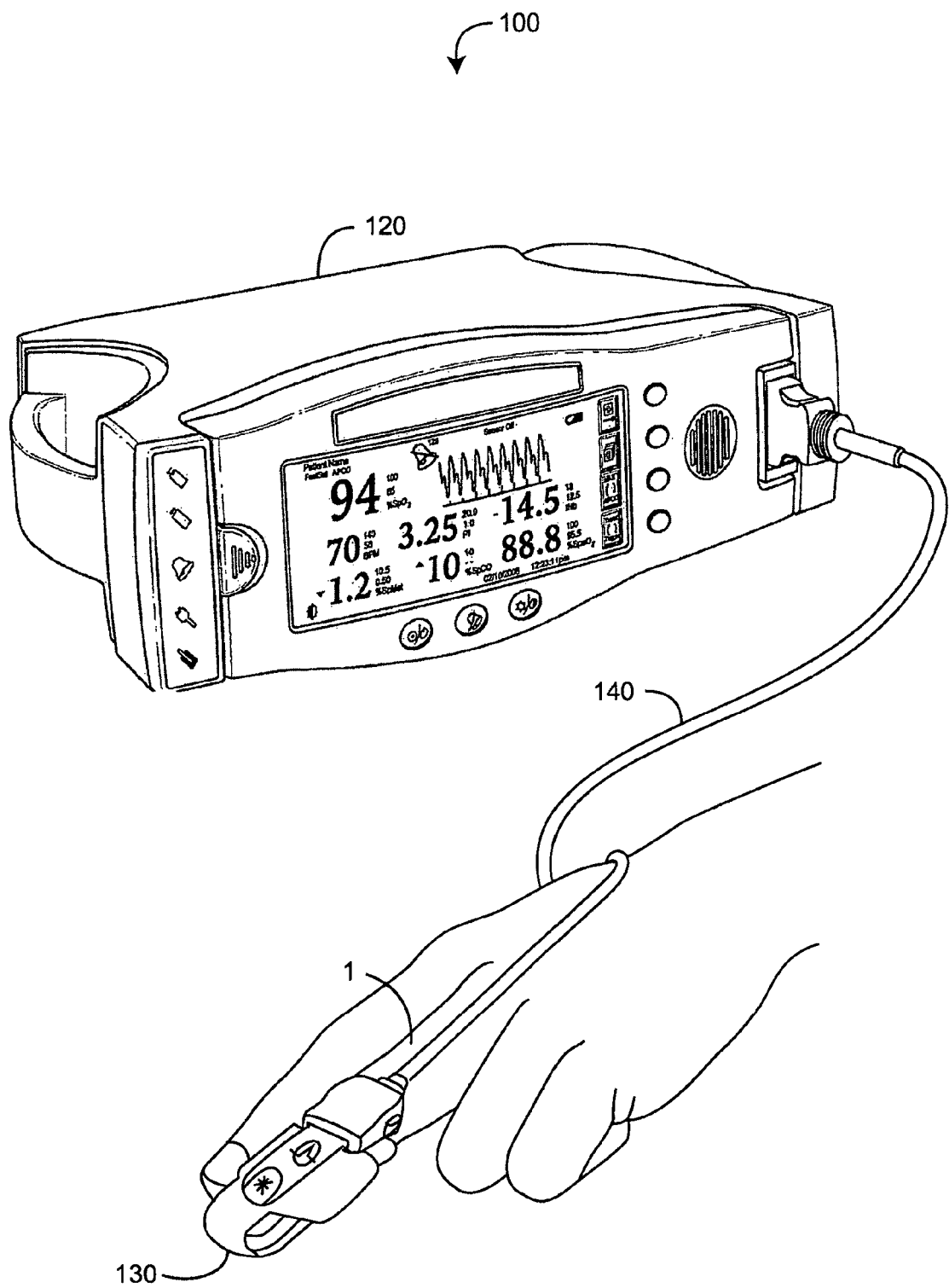
FIG. 1 is an illustration of a physiological monitoring system.
Figure 2:
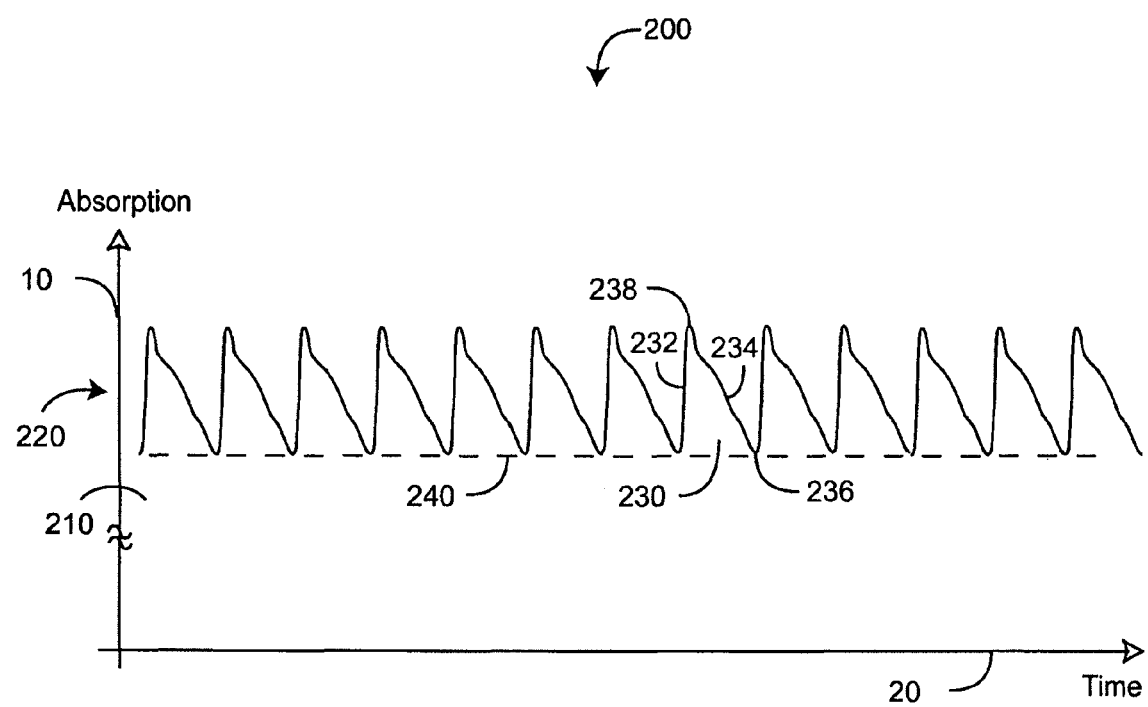
FIG. 2 is an absorption versus time graph of a standard pulse oximeter plethysmograph.
Figure 3:
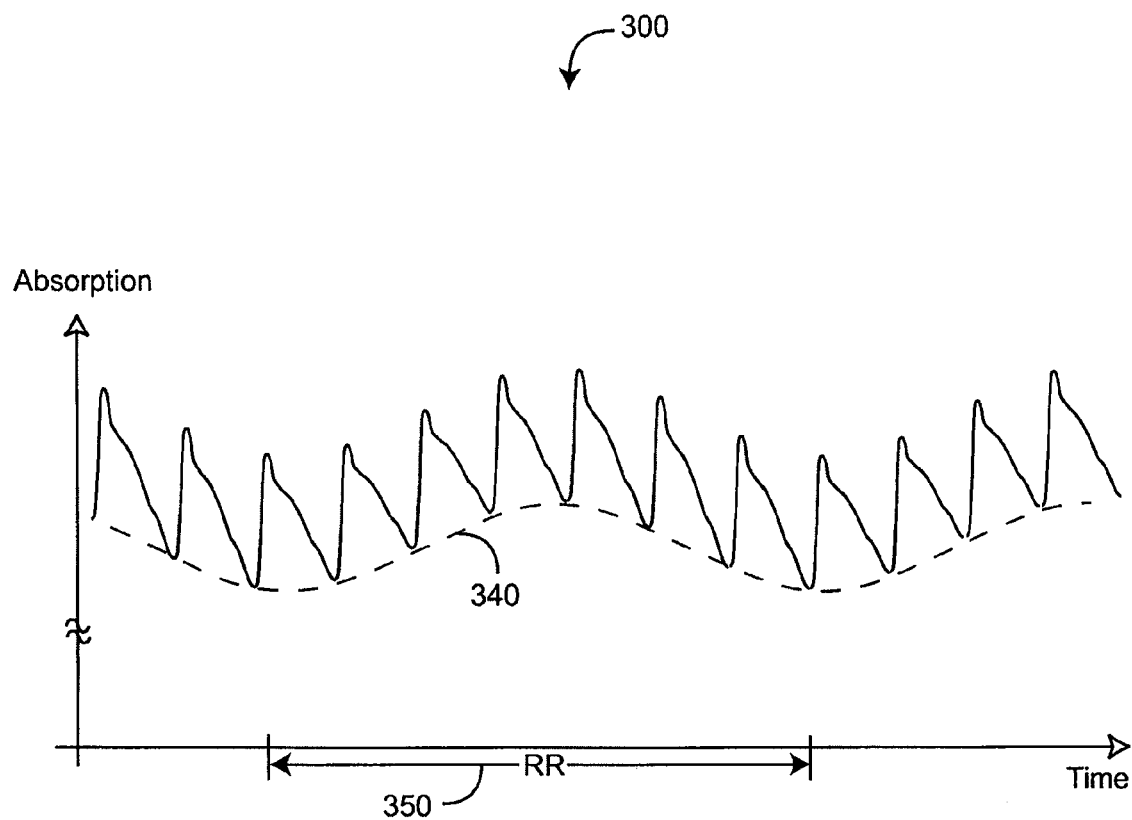
FIG. 3 is an absorption versus time graph of a plethysmograph exhibiting a respiration-induced, baseline cyclical variation.
Figure 4:
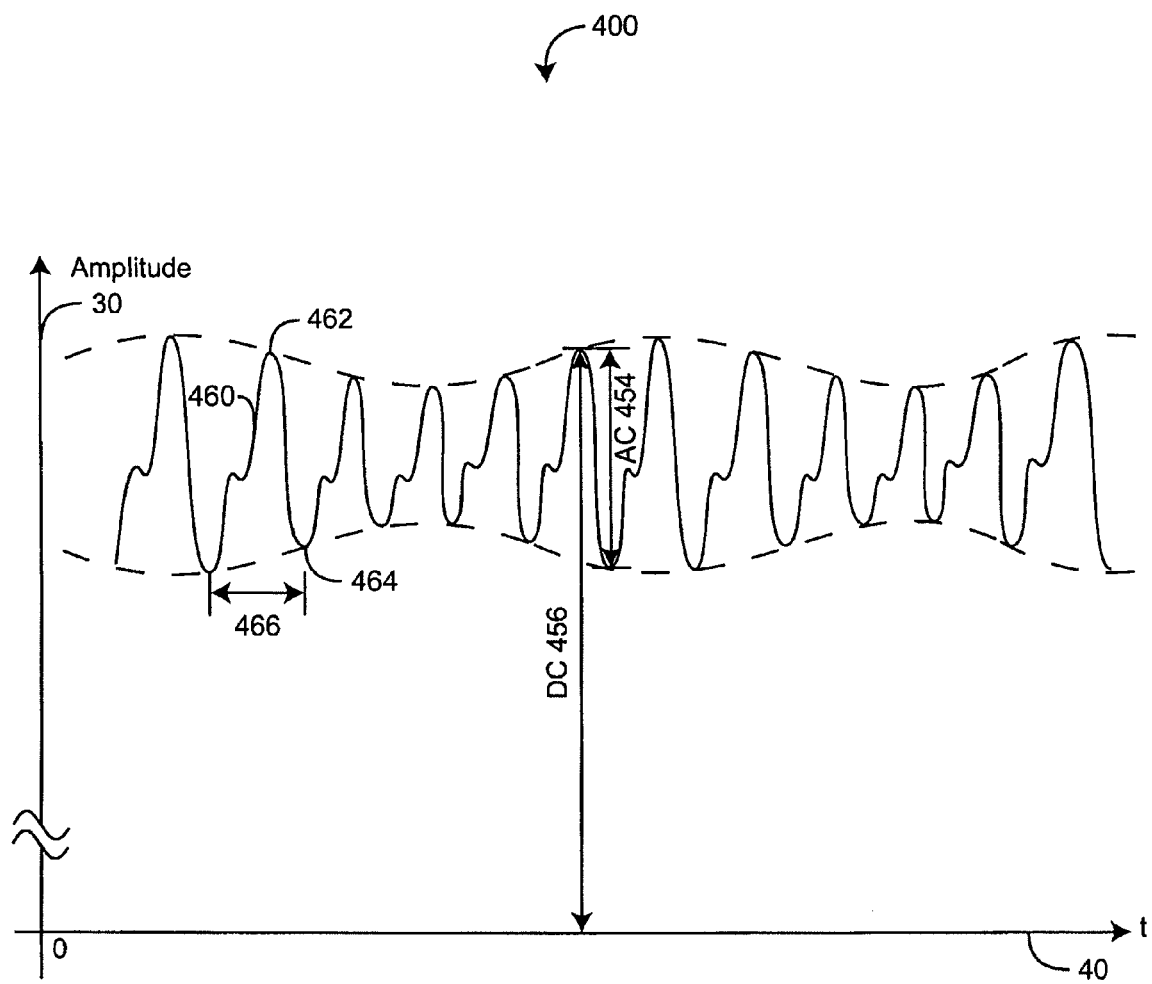
FIG. 4 is a plethysmograph illustrating measurement of a plethysmograph variability index (PVI)
Figure 5:
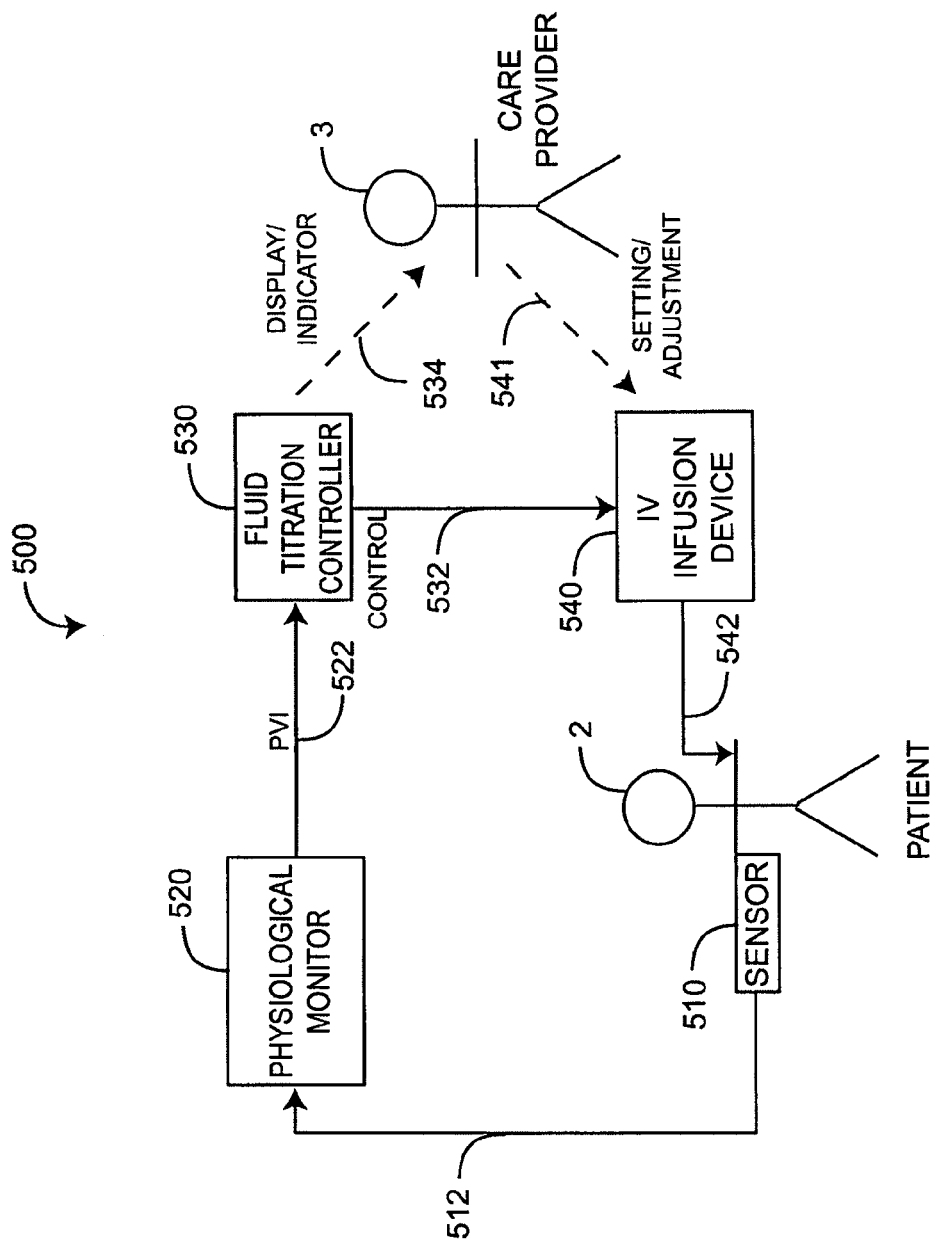
FIG. 5 is a general block diagram of an intravenous fluid titration system.

FIG. 5 illustrates a fluid titration system 500 having a sensor 510 attached to a person 2, a physiological monitor 520, a fluid titration controller 530 and an intravenous (IV) infusion device 540. Advantageously, the fluid titration system 500 utilizes a perfusion variability parameter, such as PVI described above, to regulate the administration of fluids to a person so as to control or prevent low blood volume or a hypovolemia. A noninvasive, optical sensor 510 allows a measure of tissue blood perfusion by detecting the absorption of sensor transmitted light by pulsatile blood flow within a tissue site, such as a finger, foot or ear to name a few. A sensor signal 512 responsive to that absorption is received and processed by the physiological monitor 520, which derives a plethysmograph variability index (PVI) or other measure of plethysmograph variability or, similarly, blood perfusion variability. A fluid titration controller 530 is responsive to PVI 522 and in particular to relatively large values of PVI indicating relatively large variations in perfusion index, a potential indicator of hypovolemia. The fluid titration controller 530, in turn, provides a control output 532 to an intravenous (IV) infusion device 540 so as to regulate circulating fluids and alleviate a hypovolemic condition in the person 2. The IV infusion device 540 administers a liquid solution, such as blood products or nutrient fluids injected directly into a vein (usually in the arm) at a prescribed rate over a period of time. In a closed-loop embodiment, the fluid titration controller 530 is responsive to PVI 522 or similar measure so as to start, control the rate of, or stop the infusion of fluids into the person 2. In an open-loop embodiment, the fluid titration controller 530 presents a display or other indicator 534 to a care provider 3 who manually inputs an adjustment or other setting 541 into the infusion device 540 so as to start, control the rate of, or stop the infusion of fluids into the person 2.

Figure 6:
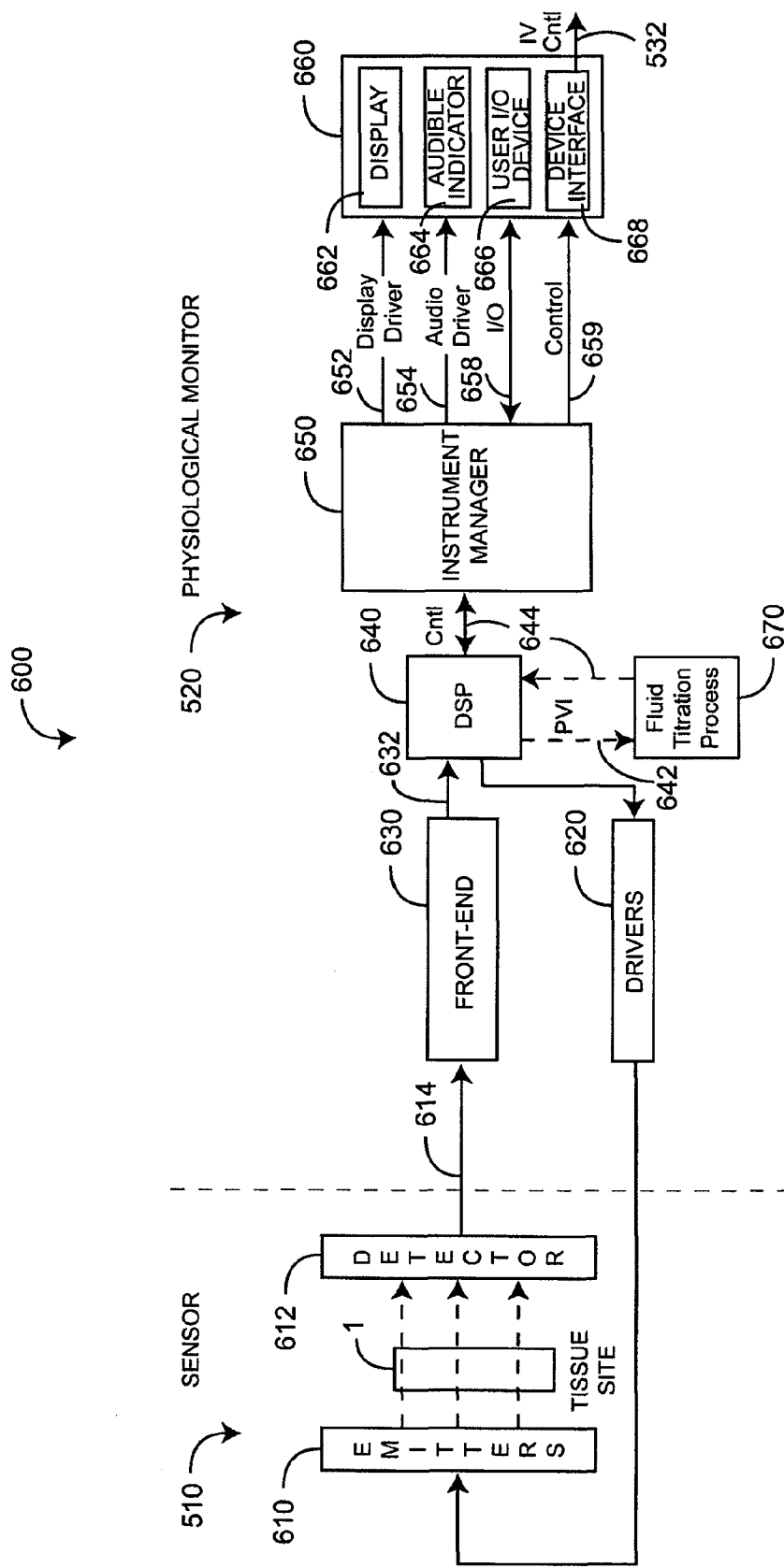
FIG. 6 is a general block diagram of a physiological monitoring system configured for a fluid titration application.

As shown in FIG. 5, the fluid titration controller 530 may be implemented in the physiological monitor 520, implemented in the IV infusion device 540, distributed between the physiological monitor 520 and the IV infusion device 540, or implemented as a standalone processing device. In an embodiment, the fluid titration controller 530 is a firmware process executed within the physiological monitor 520, as described with respect to FIG. 6, below. Physically, the physiological monitor 520 and the IV infusion device 540 may be separate units, as described with respect to FIG. 7, below, or combined into a single unit, as described with respect to FIG. 8, below.

In an embodiment, the fluid titration process 670 triggers a control output 644 so as to enable fluid flow from the IV infusion device 540 if PVI increases above a predetermined threshold or otherwise reflects that hypovolemia may no longer be indicated for a patient 2 (FIG. 5). In an embodiment, the fluid titration process 670 modifies a control output 644 so as to adjust the rate of fluid flow or total administered amount of fluid flow from the IV infusion device 540 according to changes in PVI that reflect that hypovolemia may be decreasing or increasing in severity.

Figure 7:
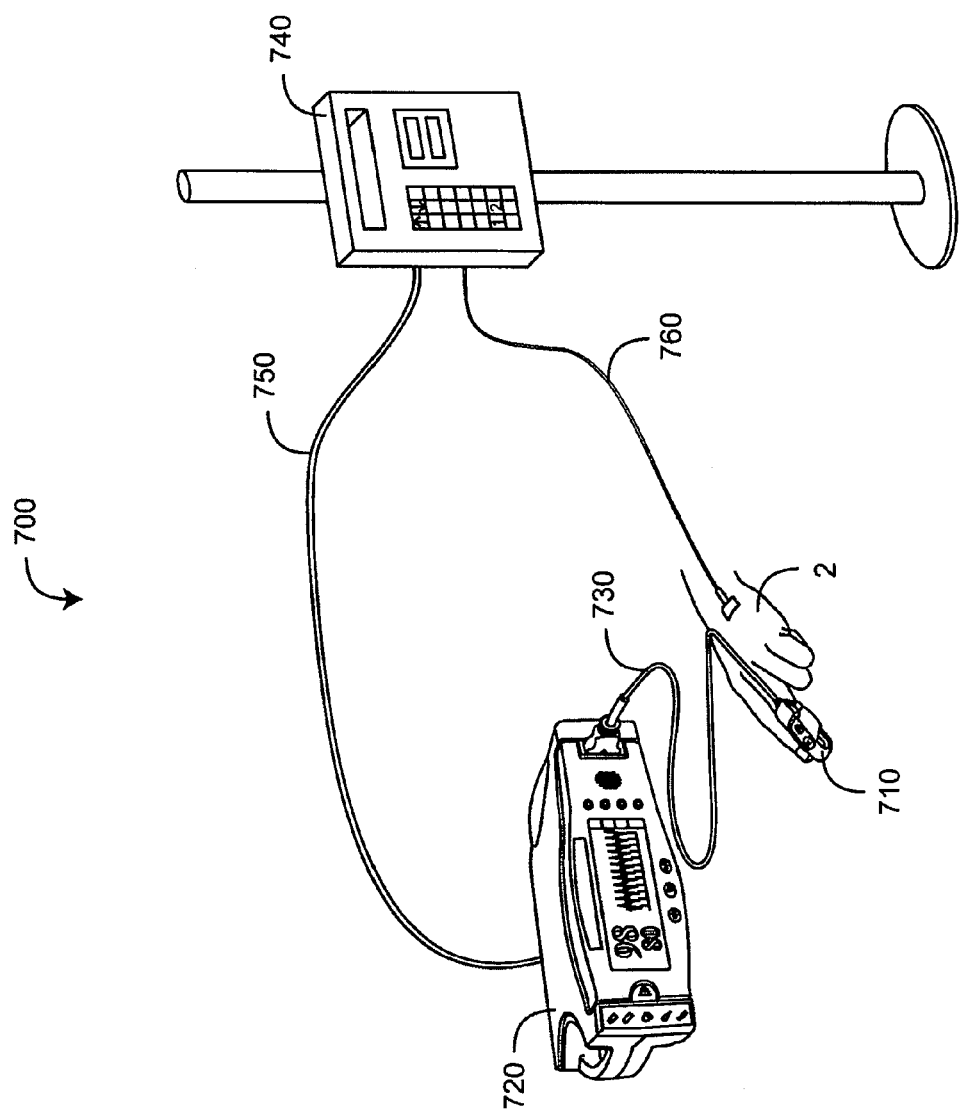
FIGS. 7-8 are illustrations of intravenous fluid titration system embodiments.

FIG. 7 illustrates a fluid titration system embodiment 700 having an optical sensor 710 attached to a person 2; a physiological monitor 720; a sensor cable 730 interconnecting the sensor 710 and monitor 720; an IV infusion device 740; a control cable 750 interconnecting the monitor 720 and infusion device 740; and an IV tube 760 also attached to the person 2. The optical sensor 710 provides a sensor signal via a sensor cable 730 to the physiological monitor 720. The physiological monitor 720 generates blood parameter measurements and processes those parameters to generate monitor and control outputs, as described with respect to FIGS. 5-6, above. In particular, the physiological monitor 720 generates control signals via a control cable 750 to the IV infusion device 740, which provides fluids to the person 2 via the IV tube 760.

Figure 8:
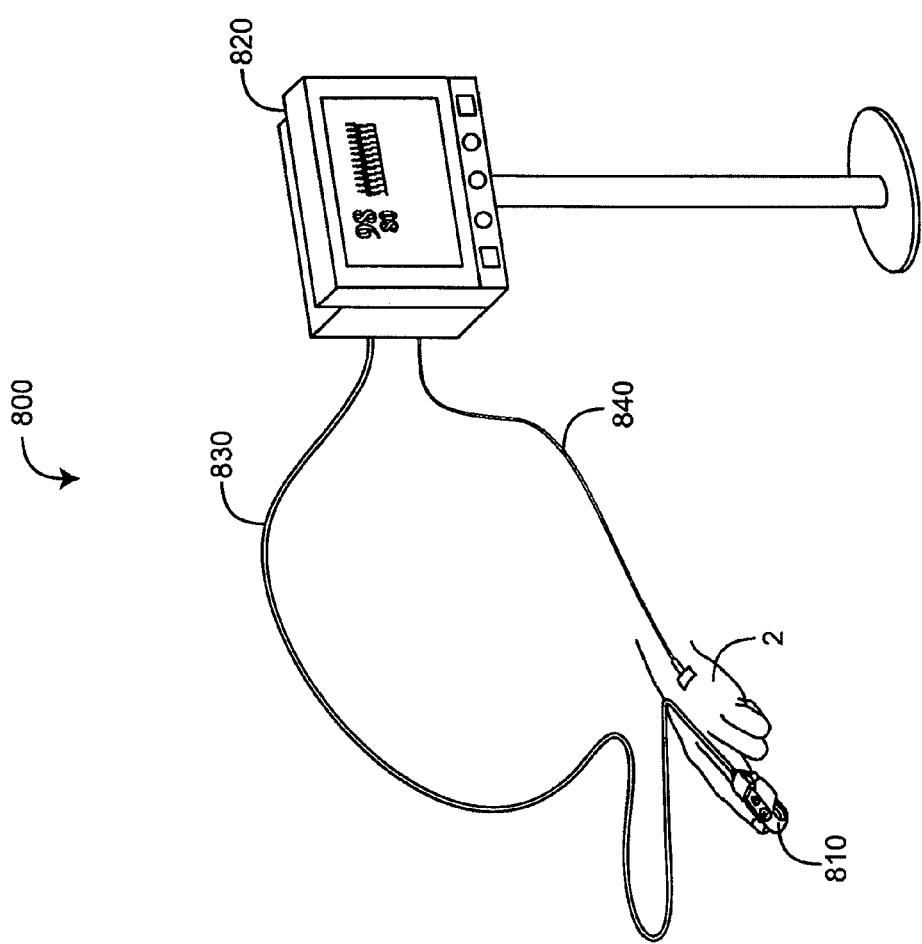

FIG. 8 illustrates another fluid titration system embodiment 800 having an optical sensor 810 and an IV tube 840 attached to a person 2 at one end and an integrated physiological monitor 820 at another end. The integrated physiological monitor 820 incorporates the functions of a physiological monitor 520 (FIG. 6) and an IV infusion device within a single unit or within physically connected units.

A fluid titration system has been disclosed in detail in connection with various embodiments. These embodiments are disclosed by way of examples only and are not to limit the scope of the claims that follow. One of ordinary skill in art will appreciate many variations and modifications.

What is claimed is:

1. A fluid titration system comprising:
    an optical sensor that transmits multiple wavelengths of optical radiation into a tissue site of a person and detects the optical radiation after attenuation by pulsatile blood flowing within the tissue site so as to generate a sensor signal responsive to the detected optical radiation;
    a physiological monitor in electrical communications with the optical sensor, the physiological monitor configured to calculate a measure of plethysmograph variability (PV) from the sensor signal; and
    an infusion device that administers a liquid solution via an intravenous (IV) connection to the person in response to the measure of PV.

2. The fluid titration system according to claim 1 further comprising a fluid titration controller, the fluid titration controller comprising:
   a PV measure input;
   a fluid control output; and
   a predetermine relationship between the PV measure input and the fluid control output,
   wherein the control output is in communication with the infusion device so as to regulate at least one of fluid flow start, rate and stop.

3. The fluid titration system according to claim 2 wherein the PV measure is responsive to changes in perfusion index (PI) over a time interval where one or more complete respiratory cycles have occurred.

4. The fluid titration system according to claim 3 further comprising:
   a digital signal processor (DSP); and
   a closed-loop fluid titration algorithm implemented in firmware executing on the DSP so as to implement the predetermined relationship.

5. The fluid titration system according to claim 4 further comprising an enclosure integrating the physiological monitor with the infusion device.

6. A fluid titration method comprising:
   deriving a plethysmograph waveform from an optical sensor attached to a person;
   determining a measure of perfusion variability corresponding to the plethysmograph waveform; and
   adjusting blood volume for the person based upon the perfusion variability metric.

7. The fluid titration method according to claim 6 wherein determining a measure of perfusion variability comprises calculating a perfusion variability index based upon a maximum perfusion measurement compared to a minimum perfusion measurement.

8. The fluid titration method according to claim 7 wherein adjusting comprises displaying an IV infusion device adjustment prompt to a care provider according to the perfusion variability index.

9. The fluid titration method according to claim 7 wherein adjusting comprises transmitting a control signal to an IV infusion device according to the perfusion variability index.

10. The fluid titration method according to claim 9 wherein the transmitting comprises at least one of:
    disabling the IV infusion device from infusing fluid when PVI is less than a first predetermined threshold; and
    enabling the IV infusion device for infusing fluid when PVI is greater than a second predetermined threshold.

11. A fluid titration system comprising:
    a sensor means for transmitting multiple wavelengths of optical radiation into a tissue site and detecting the optical radiation after attenuation by pulsatile blood flow within the tissue site;
    a physiological monitor means in communications with the sensor means for deriving a plethysmograph and calculating a measure of plethysmograph variability;
    an IV infusion device in communication with the fluid titration controller means configured to infuse a fluid into the person; and
    a titration controller means for at least partially regulating the fluid infusion in response to the measure of plethysmograph variability.

12. The fluid titration system according to claim 11 wherein the titration controller means comprises an open loop means for utilizing a care provider to adjust the IV infusion device.

13. The fluid titration system according to claim 12 wherein the open loop means comprises an indicator means for communicating infusion adjustment to a care provider.

14. The fluid titration system according to claim 11 wherein the titration controller means comprises a closed-loop means for directly controlling fluid delivery by the IV infusion device.

15. The fluid titration system according to claim 14 wherein the closed-loop means comprises an infusion control output for transmitting a control signal to the IV infusion device.

16. A fluid titration method comprising:
    deriving a plethysmograph in response to an optical sensor attached to a person, the plethysmograph having a plurality of pulses in response to the person's arterial blood flow, the pulse minima of the plethysmograph defining a baseline;
    calculating a parameter indicative of a variability of the plethysmograph;
    infusing fluid into the person via an IV; and
    regulating the infusing according to the parameter.

17. The fluid titration method according to claim 16 wherein the calculating comprises:
    determining a plurality of perfusion measures corresponding to physiologically acceptable ones of the pulses; and
    computing a perfusion variation from the perfusion measures.

18. The intravenous fluid titration method according to claim 17 wherein the infusing comprises:
    connecting an IV infusion device to the IV; and
    communicating an infusion control to the IV infusion device,
    wherein fluid flow from the IV infusion device is determined by the infusion control.

19. The intravenous fluid titration method according to claim 18 wherein the regulating comprises outputting a disabling signal on the infusion control when the variability parameter is below a predetermined threshold.

20. The intravenous fluid titration method according to claim 18 wherein the regulating comprises outputting an enabling signal on the infusion control when the parameter is above a predetermined threshold.

* * * * *

UNITED STATES PATENT AND TRADEMARK OFFICE
CERTIFICATE OF CORRECTION

PATENT NO.       : 8,048,040 B2
APPLICATION NO.  : 12/208998
DATED            : November 1, 2011
INVENTOR(S)      : Massi E. Kiani It is certified that error appears in the above-identified patent and that said Letters Patent is hereby corrected as shown below:

At column 6, line 52, in Claim 20, please delete "parameter" and insert therefore,
--variability parameter--.

Signed and Sealed this
Twenty-sixth Day of June, 2012

David J. Kappos
*Director of the United States Patent and Trademark Office*